United States Patent [19]

Urbach et al.

[11] Patent Number: 5,055,591
[45] Date of Patent: Oct. 8, 1991

[54] PROCESS FOR THE PREPARATION OF OCTAHYDROPENTA(B)PYRROLE CARBOXYLATES

[75] Inventors: Hansjörg Urbach, Kronberg/Taunus; Rainer Henning, Hattersheim am Main; Hans Wissmann, Bad Soden am Taunus; Volker Teetz, Hofheim am Taunus, all of Fed. Rep. of Germany

[73] Assignee: Hoechst Aktiengesellschaft, Frankfurt am Main, Fed. Rep. of Germany

[21] Appl. No.: 173,024

[22] Filed: Mar. 23, 1988

Related U.S. Application Data

[63] Continuation of Ser. No. 943,881, Dec. 19, 1986, abandoned, which is a continuation of Ser. No. 650,714, Sep. 14, 1984, abandoned.

[30] Foreign Application Priority Data

Sep. 16, 1983 [DE] Fed. Rep. of Germany ....... 3333455

[51] Int. Cl.$^5$ .................. C07D 207/00; C07D 209/52
[52] U.S. Cl. ................................. 548/452; 530/340; 530/342; 548/253; 562/575
[58] Field of Search ............... 530/342, 340; 548/452, 548/253; 562/575

[56] References Cited

U.S. PATENT DOCUMENTS

| 4,331,592 | 5/1982 | Wissmann et al. | 530/342 |
|---|---|---|---|
| 4,374,847 | 2/1983 | Gruenfeld . | |
| 4,508,729 | 4/1985 | Vincent et al. | 514/419 |
| 4,525,301 | 6/1985 | Henning et al. | 530/800 |
| 4,558,064 | 12/1985 | Teetz et al. . | |
| 4,558,065 | 12/1985 | Urbach et al. . | |
| 4,562,202 | 12/1985 | Urbach et al. . | |
| 4,587,258 | 5/1986 | Gold et al. | 514/412 |
| 4,591,598 | 5/1986 | Urbach et al. . | |
| 4,614,805 | 9/1986 | Urbach et al. . | |
| 4,620,012 | 10/1986 | Henning et al. . | |
| 4,659,838 | 4/1987 | Lerch . | |
| 4,668,796 | 5/1987 | Geiger et al. . | |
| 4,668,797 | 5/1987 | Urbach et al. . | |
| 4,684,662 | 8/1987 | Henning et al. . | |
| 4,691,022 | 9/1987 | Henning et al. . | |
| 4,714,708 | 12/1987 | Urbach et al. . | |
| 4,727,160 | 2/1988 | Teetz et al. . | |
| 4,808,573 | 2/1989 | Gold et al. . | |
| 4,818,749 | 4/1989 | Gold et al. . | |
| 4,822,894 | 4/1989 | Geiger et al. . | |
| 4,831,157 | 5/1989 | Gold et al. . | |
| 4,849,524 | 7/1989 | Henning et al. . | |
| 4,868,307 | 9/1989 | Barton et al. . | |
| 4,886,827 | 12/1989 | Urbach et al. . | |

FOREIGN PATENT DOCUMENTS

| 0012401 | 6/1980 | European Pat. Off. . | |
|---|---|---|---|
| 0012845 | 7/1980 | European Pat. Off. . | |
| 0018549 | 11/1980 | European Pat. Off. . | |
| 0037231A2 | 10/1981 | European Pat. Off. . | |
| 0046953 | 3/1982 | European Pat. Off. . | |
| 0049605 | 4/1982 | European Pat. Off. . | |
| 0049658 | 4/1982 | European Pat. Off. . | |
| 0050800 | 5/1982 | European Pat. Off. | 260/112.5 R |
| 0089637 | 3/1983 | European Pat. Off. . | |
| 0079022 | 5/1983 | European Pat. Off. . | |
| 0088342 | 9/1983 | European Pat. Off. . | |
| 0090362 | 10/1983 | European Pat. Off. . | |
| 2901843 | 7/1980 | Fed. Rep. of Germany . | |
| 3143946 | 5/1983 | Fed. Rep. of Germany . | |
| 3226768 | 5/1983 | Fed. Rep. of Germany . | |
| 3315464 | 10/1984 | Fed. Rep. of Germany . | |
| 3322530 | 1/1985 | Fed. Rep. of Germany . | |
| 813034 | 4/1981 | Finland . | |
| 812859 | 3/1982 | Finland . | |
| 813283 | 4/1982 | Finland . | |
| 813422 | 5/1982 | Finland . | |
| 2491469 | 4/1982 | France . | |
| 64085 | 4/1981 | Israel . | |
| 57-77672 | 5/1982 | Japan . | |
| 57-112359 | 7/1982 | Japan . | |
| 57-91974 | 8/1982 | Japan . | |
| 198702 | 8/1985 | New Zealand . | |
| 198535 | 9/1989 | New Zealand . | |
| 81/5988 | 8/1982 | South Africa . | |
| 82/8085 | 7/1983 | South Africa . | |
| 828085 | 9/1983 | South Africa . | |
| 831989 | 11/1983 | South Africa . | |
| 83/2229 | 12/1983 | South Africa . | |
| 2086390 | 5/1982 | United Kingdom . | |
| 2095682 | 10/1982 | United Kingdom . | |

OTHER PUBLICATIONS

Leonard et al., J. Am. Chem. Soc., 77, 439 (1955).
Leonard et al., J. Am. Chem. Soc., 78, 3457 (1956).
(List continued on next page.)

Primary Examiner—Lester L. Lee
Attorney, Agent, or Firm—Finnegan, Henderson, Farabow, Garrett, and Dunner

[57] ABSTRACT

The invention relates to a process for the preparation of compounds of the formula I

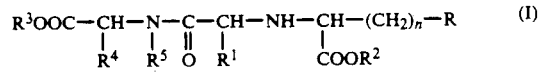

in which n is 1 or 2, R denotes hydrogen or an organic radical, $R^1$ denotes an organic radical, $R^2$ and $R^3$ are identical or different and denote hydrogen or an organic radical, and $R^4$ and $R^5$, together with the atoms bearing them, form a monocyclic, bicyclic or tricyclic heterocyclic ring system having 3 to 15 carbon atoms, which process comprises reacting compounds of the formula II defined in the description with compounds of the formula III defined in the description, in the presence of alkanephosphonic anhydrides, where appropriate eliminating radicals which have been introduced to protect other functional groups and, where appropriate, esterifying free carboxyl groups in a manner known per se.

20 Claims, No Drawings

OTHER PUBLICATIONS

Leonard et al., J. Am. Chem. Soc., 78, 3463 (1956).
Leonard et al., J. Am. Chem. Soc., 81, 5627 (1959).
Koelsch et al., J. Org. Chem., 26, 1104 (1961).
Griot et al., Helv. Chim. Acta, 42, 121 (1959).
Bonnett et al., J. Chem. Soc., 2087 (1959).
Battersby et al., J. Chem. Soc., 4333 (1958).
Rosenblatt et al., The Chemistry Of Functional Groups, Supplement F: The Chemistry of Amino, Nitroso and Nitro Compounds And Their Derivatives, Part II, S. Patai, ed., Wiley & Sons: New York 1982, pp. 1100–1104.
L. W. Haynes, Enamines, A. G. Cook, ed., Marcel Decker, Inc.: 1969, pp. 68–79, 261–269, 413.
Fieser & Fieser, Reagents For Organic Synthesis, vol. 1, pp. 644–651 (1967).
Boehme et al., Iminium Salts in Organic Chemistry, Part I (E. C. Taylor, ed.), Wiley & Sons: New York, 1976, p. 143.
S. Dayagi et al., The Chemistry Of Functional Groups, The Chemistry Of The Carbon-Nitrogen Double Bond, S. Patai, ed., Wiley & Sons: New York, 1970, p. 119.
W. Greenlee et al., J. Med. Chem., 28, 434–442 (1985).
K. Ogawa et al., J. Chem. Soc., Perkin Trans. I, 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e) (1964).
Cushman et al., Fed. Proc. 38(13), 2778–2782 (1979).
Houben-Weyl, Methoden der Organischen Chemie, 7(2b), 1403–1404 (1976).
Katritskaya, Dzh. Lagorskaya Khimia Geterosikl. Soedin., Moskow 1963, pp. 155–158.
Anderson, Jr. et al., J. Org. Chem., 43(1), 54–57 (1978).
Bertho et al., "Synthesen In Der 2–Azabicyclo[0.3.-3]-octan-Reihe", Chemische Berichte, 92(7), 2218–2235 (1959).
Farkas et al., J. Org. Chem., 22, 1261–1263 (1957).
Taylor et al., J. Org. Chem., 38(16), 2817–2821 (1973).
Taylor et al., Heterocycles, 25, 343–345 (1987).
English language translation of Mitzlaff et al., Liebig's Ann. Chem., 1713–1733 (1978).
Chem. Berichte 86: 1524–1528 (1953).
Quarterly Reviews 25: 323–341 (1971).
Chem. Abst. 49/1955/3009c.

PROCESS FOR THE PREPARATION OF OCTAHYDROPENTA(B)PYRROLE CARBOXYLATES

This application is a continuation of application Ser. No. 943,881, filed Dec. 19, 1986, now abandoned, which is a continuation of application Ser. No. 650,714, filed Sept. 14, 1984, now abandoned.

The invention relates to a process for the preparation of compounds of the formula I

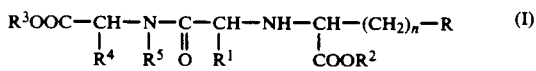

in which n is 1 or 2, R denotes hydrogen, an optionally substituted aliphatic radical having 1 to 8 carbon atoms, an optionally substituted alicyclic radical having 3–9 carbon atoms, an optionally substituted aromatic radical having 6–12 carbon atoms, an optionally substituted araliphatic radical having 7–14 carbon atoms, an optionally substituted alicyclic-aliphatic radical having 7–14 carbon atoms, or a radical $OR^a$ or $SR^a$, in which $R^a$ represents an optionally substituted aliphatic radical having 1–4 carbon atoms, an optionally substituted aromatic radical having 6–12 carbon atoms or an optionally substituted heteroaromatic radical having 5–12 ring atoms, $R^1$ denotes hydrogen, an optionally substituted aliphatic radical having 1 to 6 carbon atoms, an optionally substituted alicyclic radical having 3–9 carbon atoms, an optionally substituted alicyclic-aliphatic radical having 4–13 carbon atoms, an optionally substituted aromatic radical having 6–12 carbon atoms, an optionally substituted araliphatic radical having 7–16 carbon atoms, an optionally substituted heteroaromatic radical having 5–12 ring atoms, or the side chain, protected when necessary, of a naturally occurring α-amino acid, $R^2$ and $R^3$ are identical or different and denote hydrogen, an optionally substituted aliphatic radical having 1–6 carbon atoms, an optionally substituted alicyclic radical having 3–9 carbon atoms, an optionally substituted aromatic radical having 6–12 carbon atoms, or an optionally substituted araliphatic radical having 7–16 carbon atoms, and $R^4$ and $R^5$, together with the atoms bearing them, form a monocyclic, bicyclic or tricyclic heterocyclic ring system having 3 to 15 carbon atoms, which process comprises reacting compounds of the formula II

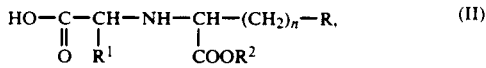

in which n, R, $R^1$ and $R^2$ have the meanings defined above, in the presence of alkanephosphonic anhydrides, with compounds of the formula III

in which $R^3$, $R^4$ and $R^5$ have the meanings defined above, where appropriate eliminating radicals which have been introduced to protect other functional groups and, where appropriate esterifying free carboxyl groups in a manner known per se.

Particularly suitable ring systems of these types are those from the following group:

Pyrrolidine (A); piperidine (B); tetrahydroisoquinoline (C); decahydroisoquinoline (D); octahydroindole (E); octahydrocyclopenta[b]pyrrole (F); 2-azabicyclo[2.2.2]octane (G); 2-azabicyclo[2.2.1]heptane (H); 2-azaspiro[4.5]decane (I); 2-azaspiro[4.4]nonane (J); spiro[(bicyclo[2.2.1]heptane)-2,3-pyrrolidine] (K); spiro[(bicyclo[2.2.2]octane)-2,3-pyrrolidine] (L); 2-azatricyclo[4.3.0.1$^{6,9}$]decane (M); decahydrocyclohepta[b]pyrrole (N); octahydroisoindole (O); octahydrocyclopenta[c]pyrrole (P); 2,3,3a,4,5,7a-hexahydroindole (Q); tetrahydrothiazole (R); 2-azabicyclo[3.1.0]hexane (S); all of which can be substituted where appropriate. However, the unsubstituted systems are preferred.

In the compounds which have several chiral atoms, all possible diastereomers, as racemates or enantiomers, or mixtures of various diastereomers, are suitable.

The suitable cyclic amino acid esters have the following structural formulae.

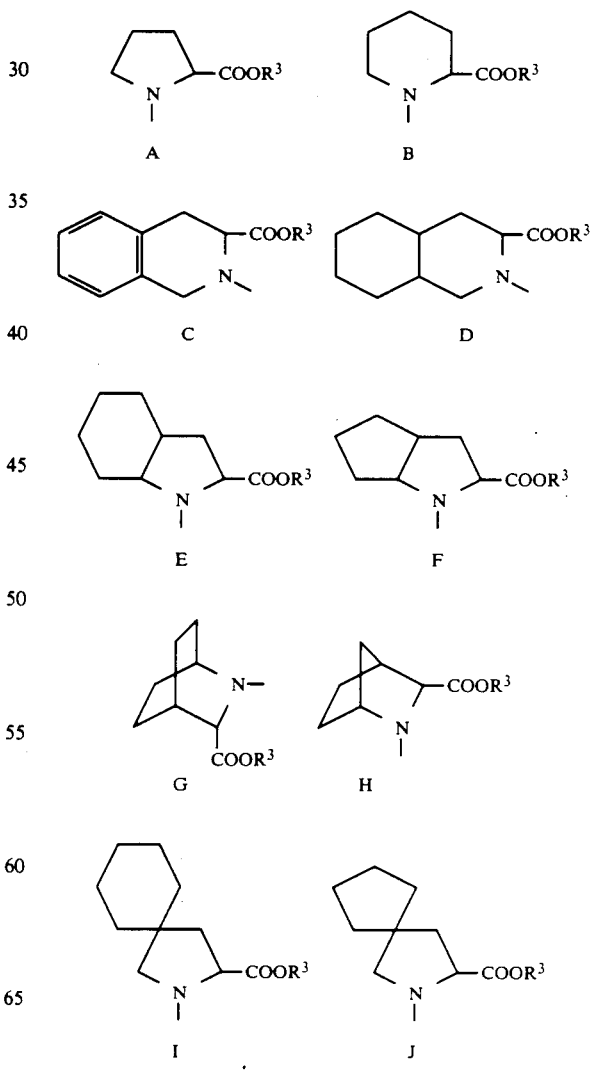

-continued

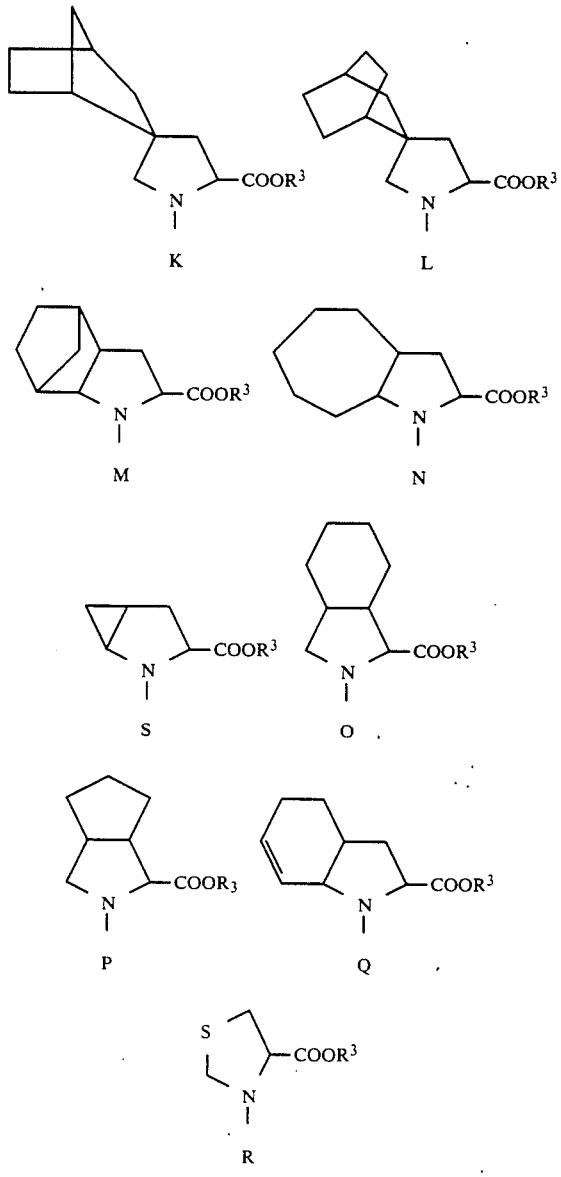

A large number of processes is known for the preparation of carboxamide and peptide bonds (see, for example, Houben-Weyl, Methoden der Organischen Chemie (Methods of Organic Chemistry), vol. XV, part II, pages 1-364, and Angew. Chemie 92, 129 (1980)). All these processes aim, with variable success, at fulfilling the criteria necessary for the synthesis of peptides, namely of freedom from racemization, of straightforward and mild procedures giving high yields and of readily accessible starting materials which are, as far as possible, non-hazardous.

A process for the preparation of compounds containing carboxamide groups by reaction of compounds containing COOH groups with compounds which contain a free $NH_2$ group, in the presence of anhydrides of alkanephosphonic acids is disclosed in U.S. Pat. No. 4,331,592.

The yields in the methods known to date for the preparation of compounds of the formula I starting from compounds of the formulae II and III (for example the HOBt-DCCI method using DMF or acetonitrile as solvents) are 50-75%. In the case of DCCI, there are difficulties associated with completely removing the dicyclohexylurea which is produced, in addition severe allergies to carbodiimides are known. Other reagents, for example other anhydrides of phosphorus acids, are suitable in principle to replace the HOBt process, but the object is to avoid using reactive reagents in order to avert side reactions (for example with the unprotected secondary amino group in the compound of the formula II).

The present process represents a new way of using the abovementioned conditions for an economic synthesis of compounds of the formula I. By means of the process according to the invention compounds of the formula II can be reacted with those of the formula III under mild conditions to give compounds of the formula I in good yields. It is a surprise that the process does not involve the occurrence of side reactions on the unprotected secondary amino group in the compounds of the formula II or the final product.

The radicals introduced to protect the functional groups can subsequently be eliminated in a customary manner.

Anhydrides of straight-chain or branched, optionally cyclic, alkanephosphonic acids having 1-8 carbon atom chain lengths, preferably up to 4 carbon atoms, are suitable for the process according to the invention.

The phosphonic anhydrides used according to the invention are stable at room temperature. They are readily soluble in most non-aqueous solvents, in particular in lipid solvents, such as chloroform or methylene chloride, but also in polar solvents, such as DMF and DMA.

Examples of anhydrides of alkanephosphonic acids which may be mentioned are the following: methanephosphonic anhydride, ethanephosphonic anhydride, n-propanephosphonic anhydride and n-butanephosphonic anhydride, in particular n-propanephosphonic anhydride.

The alkanephosphonic anhydrides can be prepared in a manner known per se, such as formulated in, for example, Houben-Weyl, Methoden der Organischen Chemie, G. Thieme Verl., Stuttgart 1963, Vol. XII/1, page 612.

A preferred embodiment comprises preparing compounds of the formula I in which n is 1 or 2, R denotes hydrogen, alkyl having 1-8 carbon atoms, alkenyl having 2-6 carbon atoms, cycloalkyl having 3-9 carbon atoms, aryl having 6-12 carbon atoms, which can be monosubstituted, disubstituted or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-acylamino, preferably $(C_1-C_4)$-alkanoylamino, methylenedioxy, carboxyl, cyano and/or sulfamoyl, alkoxy having 1-4 carbon atoms, aryloxy having 6-12 carbon atoms, which can be substituted as described above for aryl, monocyclic or bicyclic heteroaryloxy having 5-7 or 8-10 ring atoms respectively, 1 or 2 of these ring atoms being sulfur or oxygen atoms and/or 1 to 4 ring atoms being nitrogen, which can be substituted as described above for aryl, amino-$(C_1-C_4)$-alkyl, $(C_1-C_4)$-alkanoylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl-$(C_1-C_4)$-alkylamino-$(C_1-C_4)$-alkyl, $(C_1-C_4)$-alkylamino-$(C_1-C_4)$-alkyl, di-$(C_1-C_4)$-alkylamino-$(C_1-C_4)$-alkyl, guanidino-$(C_1-C_4)$-alkyl, imidazolyl, indolyl, $(C_1-C_4)$-alkylthio, $(C_1-C_4)$-alkylthio-$(C_1-C_4)$- alkyl, ($C_6$–$C_{12}$)-arylthio-($C_1$–$C_4$)-alkyl, which can be substituted in the aryl moiety as described above for aryl, ($C_6$–$C_{12}$)-aryl-($C_1$–$C_4$)-alkylthio, which can be substituted in the aryl moiety as described above for aryl, carboxy-($C_1$–$C_4$)-alkyl, carboxyl, carbamoyl, carbamoyl-($C_1$–$C_4$)-alkyl, ($C_1$–$C_4$)-alkoxycarbonyl-($C_1$–$C_4$)-alkyl, ($C_6$–$C_{12}$)-aryloxy-($C_1$–$C_4$)-alkyl, which can be substituted in the aryl moiety as described above for aryl, or ($C_6$–$C_{12}$)-aryl-($C_1$–$C_4$)-alkoxy, which can be substituted in the aryl moiety as described above for aryl, $R^1$ denotes hydrogen, alkyl having 1–6 carbon atoms, alkenyl having 2–6 carbon atoms, alkynyl having 2–6 carbon atoms, cycloalkyl having 3–9 carbon atoms, cycloalkenyl having 5–9 carbon atoms, ($C_3$–$C_9$)-cycloalkyl-($C_1$–$C_4$)-alkyl, ($C_5$–$C_9$)-cycloalkenyl-($C_1$–$C_4$)-alkyl, optionally partially hydrogenated aryl having 6–12 carbon atoms, which can be substituted as described above for R, ($C_6$–$C_{12}$)-aryl-($C_1$–$C_4$)-alkyl or ($C_7$–$C_{13}$)-aroyl-($C_1$ or $C_2$)-alkyl, both of which can be substituted as the previous aryl, monocyclic or bicyclic, optionally partially hydrogenated, heteroaryl having 5–7 or 8–10 ring atoms respectively, 1 or 2 of these ring atoms being sulfur or oxygen atoms and/or 1 to 4 ring atoms being nitrogen atoms, which can be substituted as the previous aryl, or the optionally protected side chain of a naturally occurring α-amino acid $R^1$-CH(NH$_2$)-COOH, $R^2$ and $R^3$ are identical or different and denote hydrogen, alkyl having 1–6 carbon atoms, alkenyl having 2–6 carbon atoms, di-($C_1$–$C_4$)-alkylamino-($C_1$–$C_4$)-alkyl, ($C_1$–$C_5$)-alkanoyloxy-($C_1$–$C_4$)-alkyl, ($C_1$–$C_6$)-alkoxycarbonyloxy-($C_1$–$C_4$)-alkyl, ($C_7$–$C_{13}$)-aroyloxy-($C_1$–$C_4$)-alkyl, ($C_6$–$C_{12}$)-aryloxycarbonyloxy-($C_1$–$C_4$)-alkyl, aryl having 6–12 carbon atoms, ($C_6$–$C_{12}$)-aryl-($C_1$–$C_4$)-alkyl, ($C_3$–$C_9$)-cycloalkyl or ($C_3$–$C_9$)-cycloalkyl-($C_1$–$C_4$)-alkyl, and $R^4$ and $R^5$ have the abovementioned meaning, during the reaction the free amino, alkylamino, hydroxyl, carboxyl, mercapto and/or guanidino groups present, where appropriate, in the radicals R to $R^5$ being protected in a manner known per se (cf. for example Kontakte Merck 3/79, pages 14 et seq. and 1/80, pages 23 et seq.).

A particularly preferred embodiment comprises preparing compounds of the formula I in which n is 1 or 2, R denotes ($C_1$ to $C_6$)-alkyl, ($C_2$ to $C_6$)-alkenyl, ($C_3$ to $C_9$)-cycloalkyl, amino-($C_1$–$C_4$)-alkyl, ($C_2$–$C_5$)-acylamino-($C_1$–$C_4$)-alkyl, ($C_7$–$C_{13}$)-aroylamino-($C_1$–$C_4$)-alkyl, ($C_1$–$C_4$)-alkoxycarbonylamino-($C_1$–$C_4$)-alkyl, ($C_6$ to $C_{12}$)-aryl-($C_1$–$C_4$)-alkoxycarbonylamino-($C_1$–$C_4$)-alkyl, ($C_6$ to $C_{12}$)-aryl, which can be monosubstituted, disubstituted or trisubstituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkylamino and/or methylenedioxy, or 3-indolyl, in particular methyl, ethyl, cyclohexyl, tert.-butoxycarbonylamino-($C_1$–$C_4$)-alkyl, benzoyloxycarbonylamino-($C_1$–$C_4$)-alkyl or phenyl, which can be monosubstituted or disubstituted or, in the case of methoxy, trisubstituted by phenyl, ($C_1$ or $C_2$)-alkyl, ($C_1$ or $C_2$)-alkoxy, hydroxyl, fluorine, chlorine, bromine, amino ($C_1$ to $C_4$)-alkylamino, di-($C_1$ to $C_4$)-alkylamino, nitro and/or methylenedioxy, $R^1$ denotes hydrogen or ($C_1$ to $C_6$)-alkyl, which can optionally be substituted by amino, ($C_1$ to $C_6$)-acylamino or benzoylamino, ($C_2$ to $C_6$)-alkenyl, ($C_3$ to $C_9$)-cycloalkyl, ($C_5$ to $C_9$)-cycloalkenyl, ($C_3$ to $C_7$)-cycloalkyl-($C_1$ to $C_4$)-alkyl, ($C_6$ to $C_{12}$)-aryl or partially hydrogenated aryl, each of which can be substituted by ($C_1$ to $C_4$)-alkyl, ($C_1$ or $C_2$)-alkoxy or halogen, ($C_6$–$C_{12}$)-aryl-($C_1$ to $C_4$)-alkyl or ($C_7$–$C_{13}$)-aroyl-($C_1$–$C_2$)-alkyl, both of which can be substituted in the aroyl moiety as defined previously, a monocyclic or bicyclic heterocyclic radical having 5 to 7 or 8 to 10 ring atoms respectively, 1 or 2 of these ring atoms being sulfur or oxygen atoms and/or 1 to 4 ring atoms being nitrogen atoms, or a side chain of a naturally occurring, optionally protected, α-amino acid, but particularly denotes hydrogen, ($C_1$ to $C_3$)-alkyl, ($C_2$ or $C_3$)-alkenyl, the optionally protected side chain of lysine, benzyl, 4-methoxybenzyl, 4-ethoxybenzyl, phenethyl, 4-aminobutyl or benzoylmethyl, $R^2$ and $R^3$, being identical or different radicals, denote hydrogen, ($C_1$ to $C_6$)-alkyl, ($C_2$ to $C_6$)-alkenyl or ($C_6$ to $C_{12}$)-aryl-($C_1$ to $C_4$)-alkyl, but in particular denote hydrogen, ($C_1$ to $C_4$)-alkyl or benzyl, and $R^4$ and $R^5$ have the above-mentioned meaning, during the reaction other functional groups being protected as described above.

An example of a particularly preferred process leads to compounds of the formula I in which n is 2, R denotes phenyl, $R^1$ denotes methyl, $R^2$ and $R^3$ denote identical or different ($C_1$ to $C_6$)-alkyl radicals or ($C_7$ to $C_{10}$)-aralkyl radicals such as benzyl or nitrobenzyl), and $R^4$ and $R^5$ together represent a radical of the formula

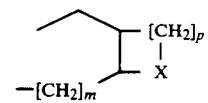

in which m=0 or 1, p=0, 1 or 2, and X=—CH$_2$—, —CH$_2$—CH$_2$— or —CH=CH—, it also being possible for a 6-membered ring formed with X to be a benzene ring.

In this context and in the following, aryl is to be understood preferably to include optionally substituted phenyl, biphenylyl or naphthyl. A corresponding statement applies to radicals derived from aryl, such as aryloxy, and arylthio. Aroyl is particularly understood to include benzoyl. Aliphatic radicals can be straight-chain or branched.

Examples of a monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, are understood to include thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. It is also possible for these radicals to be partially or completely hydrogenated.

Naturally occurring α-amino acids are described in, for example, Houben-Weyl, Methoden der Organischen Chemie, vol. XV/1 and XV/2.

Where $R^1$ represents a side chain of a protected naturally occurring α-amino acid, such as, for example, protected Ser, Thr, Asp, Asn, Glu, Gln, Arg, Lys, Hyl, Cys, Orn, Cit, Tyr, Trp, His or Hyp, the protective groups preferred are those customary in peptide chemistry (cf. Houben-Weyl, vol. XV/1 and XV/2). Where $R^1$ denotes the protected side chain of lysine, the known amino protective groups, but particularly Z, Boc or ($C_1$–$C_6$)-alkanoyl are preferred. Suitable and preferred as 0-protective groups for tyrosine are ($C_1$–$C_6$)-alkyl, in particular methyl or ethyl.

The following compounds can be obtained particularly advantageously using the process according to the invention.

N-(1-S-carboethoxy-3-phenylpropyl)-S-alanyl-S-proline benzyl ester

N-(1-R-carboethoxy-3-phenylpropyl)-S-alanyl-S-proline benzyl ester

N-(1-R,S-carboethoxy-3-phenylpropyl)-S-alanyl-S-proline benzyl ester

N-(1-S-carboethoxy-3-cyclohexylpropyl)-S-alanyl-S-proline benzyl ester

N-(1-R-carboethoxy-3-cyclohexylpropyl)-S-alanyl-S-proline benzyl ester

N-(1-R,S-carboethoxy-3-cyclohexylpropyl)-S-alanyl-S-proline benzyl ester

N-(1-S-carboethoxy-3-phenylpropyl)-$N_\epsilon$-benzyloxycarbonyl-S-lysyl-S-proline tert.-butyl ester N-(1-S-carboethoxy-3-phenylpropyl)-S-tyrosyl-S-proline benzyl ester N-(1-S-carboethoxy-3-phenylpropyl)-0-methyl-S-tyrosyl-S-proline benzyl ester N-(1-S-carboethoxy-3-phenylpropyl)-0-ethyl-S-tyrosyl-S-proline benzyl ester Benzyl N-(1-S-carboethoxy-3-phenylpropyl)-S-alanyl-S-pipecolate Benzyl N-(1-S-carboethoxy-3-cyclohexylpropyl)-S-alanyl-S-pipecolate Tert.-butyl N-(1-S-carboethoxy-3-phenylpropyl)-S-alanyl-S-1,2,3,4-tetrahydroisoquinoline-3-carboxylate Tert.-butyl N-(1-S-carboethoxy-3-cyclohexylpropyl)-S-alanyl-S-1,2,3,4-tetrahydroisoquinoline-3-carboxylate Tert.-butyl N-(1-S-carboethoxy-3-phenylpropyl)-$N_\epsilon$-benzylcarbonyl-S-lysyl-S-1,2,3,4-tetrahydroisoquinoline-3-carboxylate Tert.-butyl N-(1-S-carboethoxy-3-phenylpropyl)-0-ethyl-S-tyrosyl-S-1,2,3,4-tetrahydroisoquinoline-3-carboxylate Benzyl N-(1-S-carboethoxy-3-phenylpropyl)-S-alanyl-3S-decahydroisoquinoline-3-carboxylate Benzyl N-(1-S-carboethoxy-3-phenylpropyl)-S-alanyl-(2S,3aS,7aS)-octahydroindole-2-carboxylate Benzyl N-(1-S-carboethoxy-3-cyclohexylpropyl)-S-alanyl-(2S,3aS,7aS)-octahydroindole-2-carboxylate Tert.-butyl N-(1-S-carboethoxy-3-phenylpropyl)-$N_\epsilon$-benzyloxycarbonyl-S-lysyl-(2S,3aS,7aS)-octahydroindole-2-carboxylate Tert.-butyl N-(1-S-carboethoxy-3-cyclohexylpropyl)-$N_\epsilon$-benzyloxycarbonyl-S-lysyl-(2S,3aS,7aS)-octahydroindole-2-carboxylate Benzyl N-(1-S-carboethoxy-3-phenylpropyl)-0-methyl-S-tyrosyl-(2S,3aS,7aS)-octahydroindole-2-carboxylate Benzyl N-(1-S-carboethoxy-3-phenylpropyl)-0-ethyl-S-tyrosyl-(2S,3aS,7aS)-octahydroindole-2-carboxylate Benzyl N-(1-S-carboethoxy-4,4-dimethylphenyl)-0-alanyl-(2S,3aS,7aS)-octahydroindole-2-carboxylate Benzyl N-[1-S-carboethoxy-3-(4-fluorophenyl)propyl]-S-alanyl-(2S,3aS,7aS)-octahydroindole-2-carboxylate Benzyl N-[1-S-carboethoxy-3-(4-methoxyphenyl)propyl]-S-alanyl-(2S,3aS,7aS)-octahydroindole-2-carboxylate Benzyl N-[1-S-carboethoxy-3-(3,4-dimethoxyphenyl)propyl]-S-alanyl-(2S,3aS,7aS)-octahydroindole-2-carboxylate Benzyl N-(1-S-carboethoxy-3-cyclopentylpropyl)-S-alanyl-(2S,3aS,7aS)-octahydroindole-2-carboxylate Benzyl N-(1-S-carboethoxy-3-phenylpropyl)-S-alanyl-(2S,3aR,7aS)-octahydroindole-2-carboxylate Benzyl N-(1-S-carboethoxy-3-cyclohexylpropyl)-S-alanyl-(2S,3aR,7aS)-octahydroindole-2-carboxylate Tert.-butyl N-(1-S-carboethoxy-3-phenylpropyl)-$N_\epsilon$-benzyloxycarbonyl-S-lysyl-(2S,3aR,7aS)-octahydroindole-2-carboxylate Benzyl N-(1-S-carboethoxy-3-cyclohexylpropyl)-$N_\epsilon$-benzyloxycarbonyl-S-lysyl-(2S,3aR,7aS)-octahydroindole-2-carboxylate Benzyl N-(1-S-carboethoxy-3-phenylpropyl)-0-ethyl-S-tyrosyl-(2S,3aR,7aS)-octahydroindole-2-carboxylate Benzyl N-(1-S-carboethoxy-3-phenylpropyl)-S-alanyl-(2S,3aS,7aR)-octahydroindole-2-carboxylate Tert.-butyl N-(1-S-carboethoxy-3-phenylpropyl)-$N_\epsilon$-benzyloxycarbonyl-S-lysyl-(2S,3aR,7aR)-octahydroindole-2-carboxylate Benzyl N-(1-S-carboethoxy-3-cyclohexylpropyl)-S-alanyl-(2S,3aR,7aR)-octahydroindole-2-carboxylate Benzyl N-(1-S-carboethoxy-3-cyclohexylpropyl)-0-ethyl-S-tyrosyl-(2S,3aR,7aR)-octahydroindole-2-carboxylate Benzyl N-(1-S-carboethoxy-3-phenylpropyl)-S-alanyl-(2S,3aS,7aR)-octahydroindole-2-carboxylate Benzyl N-(1-S-carboethoxy-3-phenylpropyl)-0-ethyl-S-tyrosyl-(2S,3aS,7aS)-octahydroindole-2-carboxylate Benzyl N-(1-S-carboethoxy-4,4-dimethylphenyl)-0-alanyl-(2S,3aS,7aS)-octahydroindole-2-carboxylate Benzyl N-[1-S-carboethoxy-3-(4-fluorophenyl)propyl]-S-alanyl-(2S,3aS,7aS)-octahydroindole-2-carboxylate Benzyl N-[1-S-carboethoxy-3-(4-methoxyphenyl)propyl]-S-alanyl-(2S,3aS,7aS)-octahydroindole-2-carboxylate Benzyl N-[1-S-carboethoxy-3-(3,4-dimethoxyphenyl)propyl]-S-alanyl-(2S,3aS,7aS)-octahydroindole-2-carboxylate Benzyl N-(1-S-carboethoxy-3-cyclopentylpropyl)-S-alanyl-(2S,3aS,7aS)-octahydroindole-2-carboxylate Tert.-butyl N-(1-S-carboethoxy-3-phenylpropyl)-$N_\epsilon$-benzyloxycarbonyl-S-lysyl-(2S,3aR,6aS)-octahydrocyclopenta[b]-pyrrole-2-carboxylate Tert.-butyl N-(1-S-carboethoxy-3-cyclohexylpropyl)-$N_\epsilon$-benzyloxycarbonyl-S-lysyl-(2S,3aR,6aS)-octahydrocyclopenta[b]pyrrole-2-carboxylate Benzyl N-(1-S-carboethoxy-3-phenylpropyl)-0-ethyl-S-tyrosyl-(2S,3aR,6aS)-octahydrocyclopenta[b]pyrrole-2-carboxylate Benzyl N-(1-S-carboethoxy-3-cyclopentylpropyl)-S-alanyl-2-(2S,3aR,6aS)-octahydrocyclopenta[b]pyrrole-2-carboxylate Benzyl N-(1-S-carboethoxy-3-phenylpropyl)-S-alanyl-S-2-azabicyclo[2.2.2]octane-3-carboxylate Benzyl N-(1-S-carboethoxy-3-phenylpropyl)-0-ethyl-S-tyrosyl-S-2-azabicyclo[2.2.2]octane-3-carboxylate Benzyl N-(1-S-carboethoxy-3-cyclohexylpropyl)-S-alanyl-S-2-azabicyclo[2.2.2]octane-3-carboxylate Tert.-butyl N-(1-S-carboethoxy-3-cyclohexylpropyl)-$N_\epsilon$-benzyloxycarbonyl-S-2-azabicyclo[2.2.2]octane-3-carboxylate Tert.-butyl N-(1-S-carboethoxy-3-phenylpropyl)-$N_\epsilon$-benzyloxycarbonyl-S-lysyl-S-2-azabicyclo[2.2.2]octane-3-carboxylate Benzyl N-(1-S-carboethoxy-3-cyclopentylpropyl)-S-alanyl-S-2-azabicyclo[2.2.2]octane-3-carboxylate Benzyl N-(1-S-carboethoxy-3-phenylpropyl)-S-alanyl-3S-exo-2-azabicyclo[2.2.1]heptane-3-carboxylate Benzyl N-(1-S-carboethoxy-3-cyclohexylpropyl)-S-alanyl-3S-exo-2-azabicyclo[2.2.1]heptane-3-carboxylate Tert.-butyl N-(1-S-carboethoxy-3-phenylpropyl)-N$_\epsilon$-benzyloxycarbonyl-S-lysyl-3S-exo-2-azabicyclo[2.2.1]heptane-3-carboxylate Benzyl N-(1-S-carboethoxy-3-phenylpropyl)-S-alanyl-3S-endo-2-azabicyclo[2.2.1]heptane-3-carboxylate Benzyl N-(1-S-carboethoxy-3-cyclohexylpropyl)-S-alanyl-3S-endo-2-azabicyclo[2.2.1]heptane-3-carboxylate Tert.-butyl N-(1-S-carboethoxy-3-phenylpropyl)-N$_\epsilon$-benzyloxycarbonyl-S-lysyl-3S-endo-2-azabicyclo[2.2.1]heptane-3-carboxylate Benzyl N-(1-S-carboethoxy-3-phenylpropyl)-0-ethyl-S-tyrosyl-3S-endo-2-azabicyclo[2.2.1]heptane-3-carboxylate Benzyl N-(1-S-carboethoxy-3-phenylpropyl)-S-alanyl-2-azaspiro[4.5]decane-3-S-carboxylate Benzyl N-(1-S-carboethoxy-3-phenylpropyl)-0-ethyl-S-tyrosyl-2-azaspiro[4.5]decane-3-S-carboxylate Tert.-butyl N-(1-S-carboethoxy-3-phenylpropyl)-N$_\epsilon$-benzyloxycarbonyl-S-lysyl-2-azaspiro[4.5]decane-3-S-carboxylate Benzyl N-(1-S-carboethoxy-3-cyclohexylpropyl)-S-alanyl-2-azaspiro[4.5]decane-3-S-carboxylate Tert.-butyl N-(1-S-carboethoxy-3-cyclohexylpropyl)-N$_\epsilon$-benzyloxycarbonyl-S-lysyl-2-azaspiro[4.5]decane-3-S-carboxylate Benzyl N-(1-S-carboethoxy-3-phenylpropyl)-S-alanyl-2-azaspiro[4.4]nonane-3-S-carboxylate Benzyl N-(1-S-carboethoxy-3-phenylpropyl)-0-ethyl-S-tyrosyl-2-azaspiro[4.4]nonane-3-S-carboxylate Benzyl N-(1-S-carboethoxy-3-phenylpropyl)-N$_\epsilon$-tert.-butoxycarbonyl-S-lysyl-2-azaspiro[4.4]nonane-3-S-carboxylate Benzyl N-(1-S-carboethoxy-3-cyclohexylpropyl)-S-alanyl-2-azaspiro[4.4]nonane-3-S-carboxylate Benzyl N-(1-S-carboethoxy-3-cyclopentypropyl)-S-alanyl-2-azaspiro[4.4]nonane-3-S-carboxylate Benzyl N-(1-S-carboethoxy-3-cyclopentylpropyl)-N$_\epsilon$-tert.-butoxycarbonyl-S-lysyl-2-azaspiro[4.4]nonane-3-S-carboxylate Benzyl N-(1-S-carboethoxy-3-phenylpropyl)-S-alanyl-spiro[bicyclo[2.2.1]heptane-2,3'-pyrrolidine]-5'-S-carboxylate Benzyl N-(1-S-carboethoxy-3-phenylpropyl)-0-ethyl-S-tyrosylspiro[bicyclo[2.2.1]heptane-2,3'-pyrrolidine]-5'-S-carboxylate Tert.-butyl N-(1-S-carboethoxy-3-phenylpropyl)-N$_\epsilon$-benzyloxycarbonyl-S-lysylspiro[bicyclo[2.2.1]heptane-2,3'-pyrrolidine]-5'-S-carboxylate Benzyl N-(1-S-carboethoxy-3-cyclohexylpropyl)-S-alanylspiro[bicyclo[2.2.1]heptane-2,3'-pyrrolidine]-5'-S-carboxylate Benzyl N-(1-S-carboethoxy-3-cyclohexylpropyl)-N$_\epsilon$-tert.-butoxycarbonyl-S-lysylspiro[bicyclo[2.2.1]heptane-2,3'-pyrrolidine]-5'-S-carboxylate Benzyl N-(1-S-carboethoxy-3-phenylpropyl)-S-alanylspiro[bicyclo[2.2.2]octane-2,3'-pyrrolidine]-5'-S-carboxylate Benzyl N-(1-S-carboethoxy-3-phenylpropyl)-0-ethyl-S-tyrosylspiro[bicyclo[2.2.2]octane-2,3'-pyrrolidine]-5'-S-carboxylate Benzyl N-(1-S-carboethoxy-3-phenylpropyl)-N$_\epsilon$-tert.-butoxycarbonyl-S-lysylspiro[bicyclo[2.2.2]octane-2,3'-pyrrolidine]-5'-S-carboxylate Benzyl N-(1-S-carboethoxy-3-cyclohexylpropyl)-S-alanyl-spiro[bicyclo[2.2.2]octane-2,3'-pyrrolidine]-5'-S-carboxylate Benzyl N-(1-S-carboethoxy-3-phenylpropyl)-S-alanylazatricyclo[4.3.0.1$^{6,9}$]decane-3-S-carboxylate Benzyl N-(1-S-carboethoxy-3-phenylpropyl)-0-ethyl-S-tyrosyl-2-azatricyclo[4.3.0.1$^{6,9}$]decane-3-S-carboxylate Tert.-butyl N-(1-S-carboethoxy-3-phenylpropyl)-N$_\epsilon$-benzyloxycarbonyl-S-lysyl-2-azatricyclo[4.3.0.1$^{6,9}$]decane-3-S-carboxylate Benzyl N-(1-S-carboethoxy-3-cyclohexylpropyl)-S-alanyl-2-azatricyclo[4.3.0.1$^{6,9}$]decane-3-S-carboxylate Tert.-butyl N-(1-S-carboethoxy-3-phenylpropyl)-N$_\epsilon$-benzyloxycarbonyl-S-lysyl-2-azatricyclo[4.3.0.1$^{6,9}$]decane-3-S-carboxylate Benzyl N-(1-S-carboethoxy-3-phenylpropyl)-S-alanyl-decahydrocyclohepta[b]pyrrole-2-S-carboxylate Benzyl N-(1-S-carboethoxy-3-phenylpropyl)-0-ethyl-S-tyrosyldecahydrocyclohepta[b]pyrrole-2-S-carboxylate Tert.-butyl N-(1-S-carboethoxy-3-phenylpropyl)-N$_\epsilon$-benzyloxycarbonyl-S-lysyldecahydrocyclohepta[b]pyrrole-2-S-carboxylate Benzyl N-(1-S-carboethoxy-3-cyclohexylpropyl)-S-alanyldecahydrocyclohepta[b]pyrrole-2-S-carboxylate Benzyl N-(1-S-carboethoxy-3-cyclohexylpropyl)-N$_\epsilon$-tert.-butoxycarbonyl-S-lysyldecahydrocyclohepta[b]pyrrole-2-S-carboxylate Benzyl N-(1-S-carboethoxy-3-phenylpropyl)-S-alanyl-trans-octahydroisoindole-1-S-carboxylate Benzyl N-(1-S-carboethoxy-3-phenylpropyl)-S-alanyl-cis-octahydroisoindole-1-S-carboxylate Benzyl N-(1-S-carboethoxy-3-cyclohexylpropyl)-S-alanyl-trans-octahydroisoindole-1-S-carboxylate Benzyl N-(1-S-carboethoxy-3-cyclohexylpropyl)-S-alanyl-cis-octahydroisoindole-1-S-carboxylate Benzyl N-(1-S-carboethoxy-3-phenylpropyl)-S-alanyl-cis-octahydrocyclopenta[c]pyrrole-1-S-carboxylate Benzyl N-(1-S-carboethoxy-3-cyclohexylpropyl)-S-alanyl-cis-octahydrocyclopenta[c]pyrrole-1-S-carboxylate Benzyl N-(1-S-carboethoxy-3-cyclohexylpropyl)-N$_\epsilon$-tert.-butoxycarbonyl-S-lysyl-cis-octahydrocyclopenta[c]pyrrole-1-S-carboxylate Tert.-butyl N-(1-S-carboethoxy-3-phenylpropyl)-S-alanyl-2,3,3a,4,5,7a-hexahydroindole-cis,endo-2-S-carboxylate Tert.-butyl N-(1-S-carboethoxy-3-cyclohexylpropyl)-0-ethyl-S-tyrosyl-2,3,3a,4,5,7a-hexahydroindole-cis,exo-2-S-carboxylate Tert.-butyl N-(1-S-carboethoxy-3-cyclohexylpropyl)-S-alanyl-2,3,3a,4,5,7a-hexahydroindole-cis,endo-2-S-carboxylate Tert.-butyl N-(1-S-carboethoxy-3-phenylpropyl)-S-alanyl-thiazolidine-5-S-carboxylate Tert.-butyl N-(1-S-carboethoxy-3-cyclohexylpropyl)-S-alanylthiazolidine-5-S-carboxylate Tert.-butyl N-(1-S-carboethoxy-3-phenylpropyl)-N$_\epsilon$-benzyloxycarbonyllysylthiazolidine-5-S-carboxylate Tert.-butyl N-(1-S-carboethoxy-3-cyclohexylpropyl)-N$_\epsilon$-benzyloxycarbonyl-2-azabicyclo[3.1.0]hexane-3-S-carboxylate Benzyl N-(1-S-carboethoxy-3-phenylpropyl)-N$_\epsilon$-benzyl-oxycarbonyl-S-lysyl-2-azabicyclo[3.1.0]hexane-cis,endo-3-S-carboxylate and Benzyl N-(1-S-carboethoxy-3-cyclopentylpropyl)-S-alanyl-2-azabicyclo[3.1.0]hexane-3-carboxylate.

The reaction according to the invention is preferably carried out in a neutral or weakly alkaline medium. It is most straightforward to adjust the pH of the medium by adding aliphatic or cycloaliphatic tertiary bases, such as N-methylmorpholine, N-ethylmorpholine, or trialkylamines having up to 6 carbon atoms per alkyl radical.

All anhydrous inert solvents customary in peptide synthesis can be used as solvents, for example methylene chloride, chloroform, dimethylformamide, dimethylacetamide, dioxane, tetrahydrofuran, 1-methylpyrrolidone or dimethyl sulfoxide.

As a rule, the reaction takes place sufficiently rapidly between $-10°$ C. and $+50°$ C., preferably between $0°$ C. and room temperature. Gentle warming has no adverse effects. Higher temperatures, above about $50°$ C., are not advisable because of the danger of racemization.

The alkanephosphonic anhydrides according to the invention are preferably employed in an excess (about 2-2.5 mol of alkanephosphonic anhydride per mol of compound to be coupled). The reaction takes place without racemization (less than 2%). When using an organic or mixed organic medium, it is possible, after the reaction is complete, to remove most starting materials and impurities from the organic phase by extraction by shaking with aqueous $KHSO_4/K_2SO_4$ solution (pH 2) and then with sodium carbonate/bicarbonate solution. After evaporation of the organic phase, the resulting products remain as oils and these are converted into biologically active substances by, for example, hydrogenation (for example in the case where $R^3$ is benzyl or nitrobenzyl) or acid treatment (for example when $R^3$ is $Bu^t$).

The process according to the invention has considerable advantages, as follows:

No allergization has hitherto been observed with the acids on which the reagents for the synthesis are based. Their toxicity is low. The reagent itself, which is easy to prepare, particularly when distilled alkanephosphonic anhydrides are utilized, does not produce sparingly soluble byproducts after the synthesis, as occur, for example, with the frequently used peptide coupling employing dicyclohexylcarbodiimide.

Compared with the processes of peptide synthesis hitherto described, using activating agents based on 3- or 5-valent phosphorus, such as, for example, peptide syntheses by the phosphorazo method (Liebigs Ann. Chem. 580, page 68 (1953)), the methods of synthesis using diethyl chlorophosphite and tetraethyl pyrophosphite (J. Am. chem. Soc. 74, 5304, 5307 and 5309 (1952)) and the method of synthesis using polyphosphoric esters (Ber. 91, (1958) pages 1073–1082 or J. org. Chem. 26, 2534 (1961)), the process according to the invention has the advantage of less racemization when amino acids or peptide ester hydrochlorides are used as is customary.

The compounds of the formula I are inhibitors of angiotensin converting enzyme (ACE) or are intermediates in the preparation of inhibitors of this type, and they can be employed to control high blood pressure of a variety of etiologies. Compounds of this type are known from, for example, U.S. Pat. Nos. 4,344,949, 4,374,847, 4,350,704, European Pat. Nos. A 50,800, A 31,741, A 51,020, A 49,658, A 49,605, A 29,488, A 46,953 and A 52,870. The following German Patent Applications also relate to them: Nos. P 32 26, 768.1, P 31 51 690.4, P 32 10 496.0, P 32 11 397.8, P 32 11 676.4, P 32 27 055.0, P 32 42 151.6, P 32 46 503.3 and P 32 46 757.5.

The examples which follow are intended to illustrate the process according to the invention without restricting the invention to the substances which are mentioned here as being representative.

EXAMPLE 1

Benzyl
N-(1-S-carboethoxy-3-phenylpropyl)-S-alanyl-cis,endo-2-azabicyclo[3.3.0]octane-3-S-carboxylate
(N-ethylmorpholine as base)

31 g of benzyl S,S,S-2-azabicyclo[3.3.0]octane-3-carboxylate hydrochloride and 30 g of N-(1-S-carboethoxy-3-phenylpropyl)-S-alanine are suspended in 300 ml of methylene chloride. While stirring, 66 ml of n-propanephosphonic anhydride (in the form of a 50% strength solution in methylene chloride) and 81 g of N-ethylmorpholine are added over the course of 1 hour. The temperature is maintained between $0°$ C. and room temperature by cooling in ice. The conversion is checked by thin-layer chromatography (silica gel, system: $CHCl_3$/MeOH/HOAc $50+10+3$) after 2 hours. The mixture is left at room temperature for some hours (overnight if necessary), then evaporated in vacuo, and the reaction mixture is diluted with methylene chloride (300 ml) to a total volume of about 0.4 liter and is extracted $1 \times 150$ ml of water, $1 \times 150$ ml of water plus 90 ml of 25% strength potassium bisulfate, and $2 \times 150$ ml each time of a 5% aqueous $NaHCO_3$ solution. The organic phase is dried over a little solid sodium sulfate and is filtered. The almost colorless filtrate is evaporated. Yield: 95–100% of theory. To check the yield and purity of the product, it is possible to remove the benzyl group catalytically by the process described (methanol/Pd/C). The reaction product, N-(1-S-carboethoxy-3-phenylpropyl)-S-alanyl-cis,endo-2-azabicyclo[3.3.0]octane-3-S-carboxylic acid, crystallizes from ether in 80–90% yield (based on benzyl S,S,S-2-azabicyclo[3.3.0]octane-3-carboxylate hydrochloride).

Melting point: $109°$ C.; $[\alpha]_D^{24} = +15.7°$ (c=1, methanol).

EXAMPLE 2

Benzyl
N-(1-S-carboethoxy-3-phenylpropyl)-S-alanyl-cis,endo-2-azabicyclo[3.3.0]octane-3-S-carboxylate (with
triethylamine as base)

20 g of benzyl S,S,S-2-azabicyclo[3.3.0]octane-3-carboxylate hydrochloride are suspended in 200 ml of methylene chloride. 66 ml of triethylamine and 20 g of N-(1-S-carboethoxy-3-phenylpropyl)-S-alanine are added to this suspension. Then 44 ml of n-propanephosphonic anhydride (in the form of a 50% strength solution in methylene chloride) is added dropwise while cooling in ice and stirring. The temperature of the reaction solution is between $0°$ C. and $25°$ C. It is stirred for a further 3 hours, then diluted with 200 ml of methylene chloride, extracted by stirring with 200 ml of water, the water is separated off and the organic phase is washed consecutively with 200 ml of water plus 100 ml of 25% strength potassium bisulfate, then with 150 ml of water, and finally with 100 ml of sodium bicarbonate. The methylene chloride solution is dried over solid magnesium sulfate and is filtered. The colorless filtrate is evaporated.

Yield: about 95% of the benzyl ester.

To check the yield and purity of the product, it is possible to remove the benzyl group catalytically by the process described (methanol/Pd/C). The reaction product, N-(1-S-carboethoxy-3-phenylpropyl)-S-alanyl-cis,endo-2-azabicyclo[3.3.0]octane-3-S-carboxylic acid, crystallizes from diisopropyl ether in 90% yield based on benzyl S,S,S-2-azabicyclo[3.3.0]octane-3-carboxylate hydrochloride.

We claim:

1. A process for the preparation of a compound of the formula I

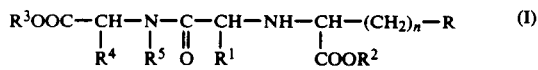

in which n is 1 or 2, R denotes hydrogen, an optionally substituted aliphatic radical having 1 to 8 carbon atoms, an optionally substituted alicyclic radical having 3-9 carbon atoms, an optionally substituted aromatic radical having 6-12 carbon atoms, an optionally substituted araliphatic radical having 7-14 carbon atoms, an optionally substituted alicyclic-aliphatic radical having 7-14 carbon atoms, or a radical $OR^a$ or $SR^a$, in which $R^a$ represents an optionally substituted aliphatic radical having 1-4 carbon atoms, an optionally substituted aromatic radical having 6-12 carbon atoms or an optionally substituted heteroaromatic radical having 5-12 ring atoms, $R^1$ denotes hydrogen, an optionally substituted aliphatic radical having 1 to 6 carbon atoms, an optionally substituted alicyclic radical having 3-9 carbon atoms, an optionally substituted alicyclic-aliphatic radical having 4-13 carbon atoms, an optionally substituted aromatic radical having 6-12 carbon atoms, an optionally substituted araliphatic radical having 7-16 carbon atoms, or an optionally substituted heteroaromatic radical having 5-12 ring atoms, $R^2$ and $R^3$ are identical or different and denote hydrogen, an optionally substituted aliphatic radical having 1-6 carbon atoms, an optionally substituted alicyclic radical having 3-9 carbon atoms, an optionally substituted aromatic radical having 6-12 carbon atoms, or an optionally substituted araliphatic radical having 7-16 carbon atoms, and $R^4$ and $R^5$, together with the atoms bearing them, form an optionally substituted octahydrocyclopenta[b]pyrrole ring system, which process comprises reacting a compound of the formula II

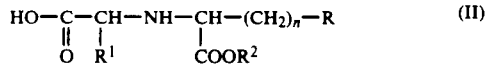

in which n, R, $R^1$ and $R^2$ have the meanings defined above, and where the amine group —NH— shown in the structure of the compound of formula II is unprotected, in the presence of at least one alkanephosphonic anhydride, with a compound of the formula III

in which $R^3$, $R^4$ and $R^5$ have the meanings defined above.

2. The process as claimed in claim 1, wherein a compound of the formula I is prepared in which n is 1 or 2, R denotes hydrogen, alkyl having 1-8 carbon atoms, alkenyl having 2-6 carbon atoms, cycloalkyl having 3-9 carbon atoms, aryl having 6-12 carbon atoms, which can be monosubstituted, disubstituted or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-acylamino, methylenedioxy, carboxyl, cyano and/or sulfamoyl, alkoxy having 1-4 carbon atoms, aryloxy having 6-12 carbon atoms, which can be substituted as described above for aryl, monocyclic or bicyclic heteroaryloxy having 5-7 or 8-10 ring atoms respectively, 1 or 2 of these ring atoms being sulfur or oxygen atoms and/or 1 to 4 ring atoms being nitrogen, which can be substituted as described above for aryl, amino-$(C_1-C_4)$-alkyl, $(C_1-C_4)$-alkanoylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl-$(C_1-C_4)$-alkylamino-$(C_1-C_4)$-alkyl, $(C_1-C_4)$-alkylamino-$(C_1-C_4)$-alkyl, di-$(C_1-C_4)$-alkylamino-$(C_1-C_4)$-alkyl, guanidino-$(C_1-C_4)$-alkyl, imidazolyl, indolyl, $(C_1-C_4)$-alkylthio, $(C_1-C_4)$-alkylthio-$(C_1-C_4)$-alkyl, $(C_6-C_{12})$-arylthio-$(C_1-C_4)$-alkyl, which can be substituted in the aryl moiety as described above for aryl, $(C_6-C_{12})$-aryl-$(C_1-C_4)$-alkylthio, which can be substituted in the aryl moiety as described above for aryl, carboxy-$(C_1-C_4)$-alkyl, carboxyl, carbamoyl, carbamoyl-$(C_1-C_4)$-alkyl, $(C_1-C_4)$-alkoxycarbonyl-$(C_1-C_4)$-alkyl, $(C_6-C_{12})$-aryloxy-$(C_1-C_4)$-alkyl, which can be substituted in the aryl moiety as described above for aryl, or $(C_6-C_{12})$-aryl-$(C_1-C_4)$-alkoxy, which can be substituted in the aryl moiety as described above for aryl, $R^1$ denotes hydrogen, alkyl having 1-6 carbon atoms, alkenyl having 2-6 carbon atoms, alkynyl having 2-6 carbon atoms, cycloalkyl having 3-9 carbon atoms, cycloalkenyl having 5-9 carbon atoms, $(C_3-C_9)$-cycloalkyl-$(C_1-C_4)$-alkyl, $(C_5-C_9)$-cycloalkenyl-$(C_1-C_4)$-alkyl, optionally partially hydrogenated aryl having 6-12 carbon atoms, which can be substituted as described above for R, $(C_6-C_{12})$-aryl-$(C_1-C_4)$-alkyl or $(C_7-C_{13})$-aroyl-$(C_1$ or $C_2)$-alkyl, both of which can be substituted as the previous aryl, monocyclic or bicyclic, optionally partially hydrogenated, heteroaryl having 5-7 or 8-10 ring atoms respectively, 1 or 2 of these ring atoms being sulfur or oxygen atoms and/or 1 to 4 ring atoms being nitrogen atoms, which can be substituted as the previous aryl, $R^2$ and $R^3$ are identical or different and denote hydrogen, alkyl having 1-6 carbon atoms, alkenyl having 2-6 carbon atoms, di-$(C_1-C_4)$-alkylamino-$(C_1-C_4)$-alkyl, $(C_1-C_5)$-alkanoyloxy-$(C_1-C_4)$-alkyl, $(C_1-C_6)$-alkoxycarbonyloxy-$(C_1-C_4)$-alkyl, $(C_7-C_{13})$-aroyloxy-$(C_1-C_4)$-alkyl, $(C_6-C_{12})$-aryloxycarbonyloxy-$(C_1-C_4)$-alkyl, aryl having 6-12 carbon atoms, $(C_6-C_{12})$-aryl-$(C_1-C_4)$-alkyl, $(C_3-C_9)$-cycloalkyl or $(C_3-C_9)$-cycloalkyl-$(C_1-C_4)$-alkyl, and $R^4$ and $R^5$ have the above-mentioned meaning, where during the reaction the free amino, alkylamino, hydroxyl, carboxyl, mercapto and/or guanidino groups present, where appropriate, in the radicals R to $R^5$ are being protected.

3. The process as claimed in claim 1, which is carried out in the presence of n-propanephosphonic anhydride.

4. The process as claimed in claim 1, wherein the reaction is carried out in an inert organic solvent in the presence of a tertiary organic amine.

5. The process as claimed in claim 1, wherein benzyl (S,S,S,S,S)-N-(1-carboethoxy-3-phenylpropyl)-alanyl-octahydrocyclopenta[b]pyrrole-2-carboxylate is prepared.

6. The process as claimed in claim 1, wherein tert.-butyl (S,S,S,S,S)-N-(1-carboethoxy-3-phenylpropyl)-alanyl-octahydrocyclopenta[b]pyrrole-2-carboxylate or another ester of (S,S,S,S,S)-N-(1-carboethoxy-3-phenylpropyl)-alanyl-octahydrocyclopenta[b]pyrrole- 2-carboxylic acid which can be cleaved by hydrogenolysis, acid or base, is prepared.

7. A process for the preparation of a compound of the formula I

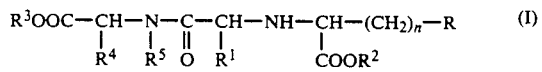

in which n is 1 or 2, R denotes hydrogen, an optionally substituted aliphatic radical having 1 to 8 carbon atoms, an optionally substituted alicyclic radical having 3–9 carbon atoms, an optionally substituted aromatic radical having 6–12 carbon atoms, an optionally substituted araliphatic radical having 7–14 carbon atoms, an optionally substituted alicyclic-aliphatic radical having 7–14 carbon atoms, or a radical $OR^a$ or $SR^a$, in which $R^a$ represents an optionally substituted aliphatic radical having 1–4 carbon atoms, an optionally substituted aromatic radical having 6–12 carbon atoms or an optionally substituted heteroaromatic radical having 5–12 ring atoms, $R^1$ denotes the side chain, protected where appropriate, of a naturally occurring α-amino acid, $R^2$ and $R^3$ are identical or different and denote hydrogen, an optionally substituted aliphatic radical having 1–6 carbon atoms, an optionally substituted alicyclic radical having 3–9 carbon atoms, an optionally substituted aromatic radical having 6–12 carbon atoms, or an optionally substituted araliphatic radical having 7–16 carbon atoms, and $R^4$ and $R^5$, together with the atoms bearing them, form an optionally substituted octahydrocyclopenta[b]pyrrole ring system, which process comprises reacting a compound of the formula II

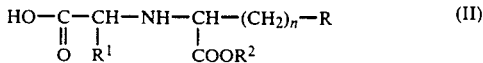

in which n, R, $R^1$ and $R^2$ have the meanings defined above, and where the amine group —NH— shown in the structure of the compound of formula II is unprotected, in the presence of at least one alkanephosphonic anhydride, with a compound of the formula III

in which $R^3$, $R^4$ and $R^5$ have the meanings defined above in a manner known per se.

8. The process as claimed in claim 7, wherein a compound of the formula I is prepared in which n is 1 or 2, R denotes hydrogen, alkyl having 1-8 carbon atoms, alkenyl having 2-6 carbon atoms, cycloalkyl having 3-9 carbon atoms, aryl having 6-12 carbon atoms, which can be monosubstituted, disubstituted or trisubstituted by ($C_1$–$C_4$)-alkyl, ($C_1$–$C_4$)-alkoxy, hydroxyl, halogen, nitro, amino, aminomethyl, ($C_1$–$C_4$)-alkylamino, di-($C_1$–$C_4$)-alkylamino, ($C_1$–$C_4$)-acylamino, methylenedioxy, carboxyl, cyano and/or sulfamoyl, alkoxy having 1-4 carbon atoms, aryloxy having 6-12 carbon atoms, which can be substituted as described above for aryl, monocyclic or bicyclic heteroaryloxy having 5-7 or 8-10 ring atoms respectively, 1 or 2 of these ring atoms being sulfur or oxygen atoms and/or 1 to 4 ring atoms being nitrogen, which can be substituted as described above for aryl, amino-($C_1$–$C_4$)-alkyl, ($C_1$–$C_4$)-alkanoylamino-($C_1$–$C_4$)-alkyl, ($C_7$–$C_{13}$)-aroylamino-($C_1$–$C_4$)-alkyl, ($C_1$–$C_4$)-alkoxycarbonylamino-($C_1$–$C_4$)-alkyl, ($C_6$–$C_{12}$)-aryl-($C_1$–$C_4$)-alkoxycarbonylamino-($C_1$–$C_4$)-alkyl, ($C_6$–$C_{12}$)-aryl-($C_1$–$C_4$)-alkylamino-($C_1$–$C_4$)-alkyl, ($C_1$–$C_4$)-alkylamino-($C_1$–$C_4$)-alkyl, di-($C_1$–$C_4$)-alkylamino-($C_1$–$C_4$)-alkyl, guanidino-($C_1$–$C_4$)-alkyl, imidazolyl, indolyl, ($C_1$–$C_4$)-alkylthio, ($C_1$–$C_4$)-alkylthio-($C_1$–$C_4$)-alkyl, ($C_6$–$C_{12}$)-arylthio-($C_1$–$C_4$)-alkyl, which can be substituted in the aryl moiety as described above for aryl, ($C_6$–$C_{12}$)-aryl-($C_1$–$C_4$)-alkylthio, which can be substituted in the aryl moiety as described above for aryl, carboxy-($C_1$–$C_4$)-alkyl, carboxyl, carbamoyl, carbamoyl-($C_1$–$C_4$)-alkyl, ($C_1$–$C_4$)-alkoxycarbonyl-($C_1$–$C_4$)-alkyl, ($C_6$–$C_{12}$)-aryloxy-($C_1$–$C_4$)-alkyl, which can be substituted in the aryl moiety as described above for aryl, or ($C_6$–$C_{12}$)-aryl-($C_1$–$C_4$)-alkoxy, which can be substituted in the aryl moiety as described above for aryl, $R^1$ denotes the optionally protected side chain of a naturally occurring α-amino acid $R^1$—CH($NH_2$)—COOH, $R^2$ and $R^3$ are identical or different and denote hydrogen, alkyl having 1-6 carbon atoms, alkenyl having 2-6 carbon atoms, di-($C_1$–$C_4$)-alkylamino-($C_1$–$C_4$)-alkyl, ($C_1$–$C_5$)-alkanoyloxy-($C_1$–$C_4$)-alkyl, ($C_1$–$C_6$)-alkoxycarbonyloxy-($C_1$–$C_4$)-alkyl, ($C_7$–$C_{13}$)-aroyloxy-($C_1$–$C_4$)-alkyl, ($C_6$–$C_{12}$)-aryloxycarbonyloxy-($C_1$–$C_4$)-alkyl, aryl having 6-12 carbon atoms, ($C_6$–$C_{12}$)-aryl-($C_1$–$C_4$)-alkyl, ($C_3$–$C_9$)-cycloalkyl or ($C_3$–$C_9$)-cycloalkyl-($C_1$–$C_4$)-alkyl, and $R^4$ and $R^5$ have the above-mentioned meaning, where during the reaction the free amino, alkylamino, hydroxyl, carboxyl, mercapto and/or guanidino groups present, where appropriate, in the radicals R to $R^5$ are being protected.

9. The process as claimed in claim 7, which is carried out in the presence of n-propanephosphonic anhydride.

10. The process as claimed in claim 7, wherein the reaction is carried out in an inert organic solvent in the presence of a tertiary organic amine.

11. The process as claimed in claim 7, wherein benzyl (S,S,S,S,S)-N-(1-carboethoxy-3-phenylpropyl)-alanyl-octahydrocyclopenta[b]pyrrole-2-carboxylate is prepared.

12. The process as claimed in claim 7, wherein tert.-butyl (S,S,S,S,S)-N-(1-carboethoxy-3-phenylpropyl)-alanyl-octahydrocyclopenta[b]pyrrole-2-carboxylate or another ester of (S,S,S,S,S)-N-(1-carboethoxy-3-phenylpropyl)-alanyl-octahydrocyclopenta[b]pyrrole-2-carboxylic acid which can be cleaved by hydrogenolysis, acid or base, is prepared.

13. The process as claimed in claim 1, wherein said process is carried out in a neutral or weakly alkaline medium.

14. The process as claimed in claim 13, wherein an aliphatic or cycloaliphatic tertiary base is added.

15. The process as claimed in claim 7, wherein said process is carried out in a neutral or weakly alkaline medium.

16. The process as claimed in claim 15, wherein an aliphatic or cycloaliphatic tertiary base is added.

17. The process as claimed in claim 1, wherein methylene chloride is employed as a solvent.

18. The process as claimed in claim 7, wherein methylene chloride is employed as a solvent.

19. The process as claimed in claim 1, further comprising the step(s) of eliminating radicals which have been introduced to protect one or more functional groups and/or esterifying free carboxyl groups.

20. The process as claimed in claim 7, further comprising the step(s) of eliminating radicals which have been introduced to protect one or more functional groups and/or esterifying free carboxyl groups.

* * * * *

UNITED STATES PATENT AND TRADEMARK OFFICE
CERTIFICATE OF CORRECTION

PATENT NO. : 5,055,591
DATED : October 8, 1991
INVENTOR(S) : Hansjorg Urbach, et. al.

It is certified that error appears in the above-indentified patent and that said Letters Patent is hereby corrected as shown below:

Title Page, Title, change "OCTAHYDROPENTA(B)PYRROLE CARBOXYLATES" to --N-ALKYLATED DIPEPTIDES AND THEIR ESTERS--.

Claim 2, column 14, line 54, delete "being".

Claim 7, column 15, line 48, delete "in a manner known per se".

Claim 8, column 16, line 29, delete "being".

Signed and Sealed this

Fifteenth Day of June, 1993

Attest:

MICHAEL K. KIRK

Attesting Officer

Acting Commissioner of Patents and Trademarks